| United States Patent [19] | [11] 3,931,247 |
| --- | --- |
| Pelosi, Jr. | [45] Jan. 6, 1976 |

[54] 5-(SUBSTITUTED)PHENYLFURFURYL ALCOHOLS

[75] Inventor: Stanford S. Pelosi, Jr., Norwich, N.Y.

[73] Assignee: Morton-Norwich Products, Inc., Norwich, N.Y.

[22] Filed: Dec. 11, 1974

[21] Appl. No.: 531,465

[52] U.S. Cl. ........ 260/347.2; 260/347.3; 260/347.7; 260/347.8; 424/285
[51] Int. Cl.² .................................... C07D 307/42
[58] Field of Search .......... 260/347.2, 347.3, 347.7, 260/347.8

[56] References Cited
UNITED STATES PATENTS
3,458,523  7/1969  Szmuszkovicz ................ 260/347.8

OTHER PUBLICATIONS
Oleinik et al., Chem. Abstracts, Vol. 78, item 43169, (Feb. 1973).

*Primary Examiner*—Harry I. Moatz
*Attorney, Agent, or Firm*—Anthony J. Franze

[57] ABSTRACT

A series of 5-(substituted)phenylfurfuryl alcohols are useful as anti-inflammatory agents.

10 Claims, No Drawings

5-(SUBSTITUTED)PHENYLFURFURYL ALCOHOLS

This invention is concerned with chemical compounds. More particularly it is directed to a series of 5-(substituted)phenylfuryl alcohols of the formula:

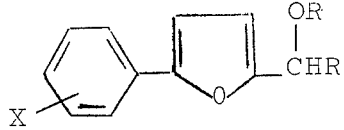

wherein X is 4-nitro, 3,4 dichloro, 3-trifluoromethyl, 4-amino, 4-acetamido, 4-methylsulfonyl, 4-cyano, or 4-chloro and R is methyl, ethyl or chloromethyl.

The members of this series of compounds possess pharmacologic activity. They are particularly useful as anti-inflammatory agents as evidenced by their ability to inhibit edema induced in rats by the administration of carrageenin. Thus, when administered at a dose of 300 mg/kg suspended in a vehicle such as aqueous methyl cellulose per os to rats receiving carrageenin, edema associated with that substance is inhibited [Winter et al., P.S.E.B.M. (14:544 (1964)].

The method which is currently preferred for the preparation of the compounds of this invention consists in the reduction of the corresponding ketone. This method is illustrated in the following examples.

EXAMPLE I

α-Methyl-5-(p-nitrophenyl)furfuryl Alcohol

Sodium borohydride (9.0 g, 0.34 mole) was added in portions to a stirred mixture of 55 g (0.24 mole) of methyl 5-(p-nitrophenyl)-2-furyl ketone in 700 ml of methanol at 20°–25° over 45 minutes. The mixture was stirred at ambient temperature for 4 hours and allowed to stand overnight. Some insoluble material was removed by filtration and discarded. The filtrate was poured into a mixture of ice and water (3 liters) and made acidific with 5% aqueous HCl. The brown oil which was deposited solidified on standing and was collected by filtration to give 56 g (100%) of title compound. Recrystallization from a cyclohexane-benzene mixture gave an analytical sample, m.p. 69.5°–70.5°.

Anal. Calcd. for $C_{12}H_{11}NO_4$: C, 61.80; H, 4.75; N, 6.01. Found: C, 61.95; H, 4.90; N, 5.94.

EXAMPLE II 5-(3,4-Dichlorophenyl)-α-methylfurfuryl Alcohol

A. A mixture of 81 g (0.50 mole) of 3,4-dichloroaniline, 100 ml of water and 75 ml of conc. HCl was heated on a steam bath to ca. 70°, and 150 ml of conc. HCl was added. White crystals separated and the mixture was cooled to 0°. A solution of 35 g (0.50 mole) of sodium nitrite in 150 ml of water was added at 0°–5° over 25 min and stirring was continued at 0°–5° for 1 hour. A solution of 55 g (0.50 mole) of methyl 2-furyl ketone in 50 ml of acetone was added quickly followed by the dropwise addition over 10 minutes at 4°–5° of a solution of 10 g (0.06 mole) of cupric chloride dihydrate in 20 ml of water. The cooling bath was removed, and the green solution was stirred overnight at ambient temperature. The solid which was deposited was collected by filtration and washed with water. Recrystallization from ca. 800 ml of MeOH gave 45 g (35%) of 5-(3,4-dichlorophenyl)-2-furyl methyl ketone A. Two additional recrystallizations from MeOH gave an analytical sample, m.p. 114°–117°.

Anal. Calcd. for $C_{12}H_8Cl_2O_2$: C, 56.50; H, 3.16. Found: C, 56.17; H, 3.14.

B. Sodium Borohydride (1.5 g, 0.04 mole) was added in portions to a stirred mixture of 15 g (0.059 mole) of 5-(3,4-dichlorophenyl)-2-furyl methyl ketone and 125 ml of MeOH at 15°–20° over 30 minutes. The mixture was stirred at ambient temperature for 3 hours. Some insoluble material was removed by filtration and set aside. The filtrate was poured into 300 ml of ice-$H_2O$ mixture and made acidic with dilute HCl. The oil which was deposited solidified and was collected by filtration. Recrystallization from n-hexane gave 11 g (73%) of title compound, m.p. 82.5°–83.5°.

Anal. Calcd. for $C_{12}H_{10}Cl_2O_2$: C, 56.05; H, 3.92. Found: C, 56.20; H, 4.00.

EXAMPLE III 5-(m-Trifluoromethylphenyl)-α-(methylfurfuryl Alcohol

A. A mixture of 322 g (2.0 moles) of 3-aminobenzotrifluoride, 690 ml of concentrated hydrochloric acid and 260 ml of water was heated with steam for 20 minutes at 80° and then cooled to 0°. An additional 200 ml of water was added to aid in stirring. A solution of 138 g (2.0 moles) of sodium nitrite in 500 ml of water was added dropwise while maintaining the temperature between 0°–5° by means of an ice bath. The reaction mixture was stirred for 30 minutes and then filtered to remove a small amount of solid which was discarded. The pH of the solution was adjusted to ca. 4 by the addition of 900 ml of saturated sodium acetate solution. A solution of 220 g (2.0 moles) of methyl-2-furyl ketone in 200 ml of acetonitrile was added followed by a solution of 40 g of $CuCl_2 \cdot 2H_2O$ in 100 ml of water. The reaction was stirred at 5°–15° for 1 hour and then warmed to room temperature becoming slightly exothermic. The reaction mixture was controlled below 33° by means of an ice bath. After 1¼ hour the reaction was no longer exothermic and was stirred at room temperature overnight. The oil mixture was extracted with 2 × 750 ml and 1 × 500 ml portions of ether. The ethereal extracts were combined and washed with 2000 ml of 5% sodium carbonate solution, with 1500 ml of water and then dried over magnesium sulfate. The ether was removed on the calab evaporator and the residue refrigerated for 72 hours. The solid which was formed was filtered, washed with pet ether and air-dried to yield 174 g. The crude product was recrystallized from 2500 ml of hexane/charcoal to yield 112 g (24%) of 5-(m-trifluoromethylphenyl)-2-furyl methyl ketone. An analytical sample was prepared by recrystallizing a sample of crude product twice from hexane/charcoal, m.p. 105°–109°.

Anal. Calcd. for $C_{13}H_9F_3O_2$: C, 61.43; H, 3.57. Found: C, 61.26; H, 3.66.

B. To a stirring mixture of 46 g (0.18 mole) of 5-(m-trifluoromethylphenyl)-2-furyl methyl ketone and 350 ml of methanol was added portionwise 4.53 g (0.12 mole) of $NaBH_4$ while maintaining the temperature between 15°–20° by means of an ice bath. The ice bath was removed and the resulting solution stirred at ambient temperature for 3 hours and then allowed to stand at room temperature overnight. The solution was poured into 2000 ml of ice water to give a semisolid after scratching and cooling. The mixture was refrigerated overnight and the solid was collected by filtration. The solid was dissolved in methanol, treated with charcoal, filtered, and poured onto ice. The product which formed was filtered and dried in a desiccator over KOH to yield 29 g (61%). An analytical sample was prepared by recrystallizing a sample from pet ether/charcoal, m.p. 56°–57°C.

Anal. Calcd. for $C_{13}H_{11}F_3O_2$: C, 60.94; H, 4.33. Found: C, 60.60; H, 4.35.

EXAMPLE IV

α-Methyl-5-(p-aminophenyl)furfuryl Alcohol

A mixture of 79 g (0.34 mole) of the compound of Example I, 1 tsp. of 5% Pd/C, 50% $H_2O$, and 500 ml of methanol was shaken under hydrogen pressure with the theoretical amount of $H_2$ being absorbed. The catalyst was removed by filtration, and the filtrate was taken to near dryness on a Calab evaporator. The resulting solid was filtered and air-dried to yield 49 g (71%) of title compound. An analytical sample was prepared by recrystallizing a sample twice from ethanol/charcoal, m.p. 100°–104°.

Anal. Calcd. for $C_{12}H_{13}NO_2$: C, 70.92; H, 6.59; N, 6.89. Found: C, 71.10; H, 6.56; N, 6.78.

EXAMPLE V 5-(p-Acetamidophenyl)-α-methylfurfuryl Alcohol

A. A mixture of 58 g (0.25 mole) of methyl 5-(p-nitrophenyl)-2-furyl ketone, 2 tsp. of Raney Ni and 750 ml of ethanol was shaken under hydrogen pressure for one hour with the theoretical amount of $H_2$ being absorbed. An additional 2000 ml of ethanol was added to the reaction mixture. The mixture was heated to reflux and the catalyst was removed by filtration. The filtrate was treated with ethereal HCl and the resulting solid was filtered and air-dried to yield 41 g (8.15%) of methyl 5-(p-aminophenyl)-2-furyl ketone. An analytical sample was prepared by drying a sample at room temperature in the vacuum pistol, m.p. scinters above 160°.

Anal. Calcd. for $C_{11}H_{11}NO_2.HCl$: C, 60.64; H, 5.09. Found: C, 60.63; H, 5.22.

B. A mixture of 5.0 g (0.0248 mole) of methyl 5-(p-aminophenyl)-2-furyl ketone and 75 ml of acetic anhydride was heated at 70°–90° for 2 hours. The excess acetic anhydride was removed on a Calab evaporator, and the residual solid was recrystallized from ethyl acetate to yield 4.4 g (73%) of methyl 5-(p-acetamidophenyl)-2-furyl ketone. An analytical sample was prepared by drying a sample in the vacuum pistol at the temperature of refluxing chloroform, m.p. 214°–215°.

Anal. Calcd. for $C_{14}H_{13}NO_3$: C, 69.12; H, 5.39; N, 5.76. Found: C, 69.14; H, 5.41; N, 5.76.

C. To a stirring mixture of 22 g (0.090 mole) of methyl 5-(p-acetamido-phenyl)-2-furyl ketone and 345 ml of 95% dioxane/$H_2O$ was added portionwise 3.4 g (0.090 mole) of $NaBH_4$ while maintaining the temperature at 15°–20°. The resulting mixture was stirred overnight at room temperature and then added to ice/water. The solid was filtered and dried at 60° to yield 21 g (95%), m.p. 175°–177°, of title compound.

Anal. Calcd. for $C_{14}H_{15}NO_3$: C, 68.55; H, 6.16; N, 5.71. Found: C, 68.32; H, 6.06; N, 5.60.

EXAMPLE VI

α-Methyl-5-(p-methylsulfonylphenyl)furfuryl Alcohol

A. A mixture of 200 g (1.16 mole) of p-aminophenyl methyl sulfone, 405 ml of concentrated hydrochloric acid, and 150 ml of water was heated at 80° for 20 minutes and then cooled to 0°. A solution of 80 g (1.16 mole) of sodium nitrite in 270 ml of water was added dropwise while maintaining the temperature between 0°–5° by means of an ice bath. The near solution was kept at 0° for 15 minutes. A solution of 129 g (1.16 mole) of methyl 2-furyl ketone in 125 ml of acetonitrile was added followed by a solution of 30 g of $CuCl_2.2H_2O$ in 100 ml of water. The reaction, after stirring in the cold for one hour, was allowed to warm to room temperature at which time it became exothermic and was controlled below 55° by means of an ice bath. The reaction, after stirring overnight at room temperature, was treated with 500 ml of ether with a solid forming. The solid was filtered, washed with dilute NaOH solution, and refluxed in acetonitrile with the insoluble material being removed by filtration. The filtrate was again heated to reflux and water was added to the "cloud point". Upon cooling an oil formed from which the acetonitrile was decanted. The acetonitrile was again treated with water and the resulting solid was filtered and recrystallized from ethyl acetate/charcoal and airdried to yield 28 g (9%) of 5-(p-methylsulfonylphenyl)-2-furyl methyl ketone. An analytical sample was prepared by drying a sample in the vacuum pistol at the temperature of refluxing $CHCl_3$, m.p. 160°–164°.

Anal. Calcd. for $C_{13}H_{12}O_4S$: C, 59.08; H, 4.58. Found: C, 58.89; H, 4.61.

B. A mixture of 2.0 g (0.0076 mole) of 5-(p-methylsulfonylphenyl)-2-furyl ketone and 40 ml of 95% of dioxane/$H_2O$ was treated portionwise with 0.29 g (0.0076 mole) of $NaBH_4$ while maintaining the temperature at 15°–20° by means of an ice bath. The resulting solution was stirred at room temperature for 2 hours, added to ice/$H_2O$ and the resulting precipitate filtered and dried in the vacuum pistol at room temperature to yield 1.3 g (64%), m.p. 118°–120°, of title compound.

Anal. Calcd. for $C_{13}H_{14}SO_4$: C, 58.63; H, 5.30. Found: C, 58.32; H, 5.31.

EXAMPLE VII

4-[5-(1-Hydroxyethyl)-2-furyl]benzonitrile

A. A mixture of 50 g (0.42 mole) of p-aminobenzonitrile, 146 ml of concentrated hydrochloric acid, and 106 ml of $H_2O$ was heated at 80° for for 20 minutes and then cooled to 0°. A solution of 29 g (0.42 mole) of sodium nitrite in 105 ml of $H_2O$ was added dropwise while maintaining the temperature at 0°–5° by means of an ice bath. The reaction was kept at 0° for 45 minutes. A solution of 47 g (0.42 mole) of methyl 2-furyl ketone in 43 ml of acetonitrile was added followed by a solution of 10 g of $CuCl_2.2H_2O$ in 50 ml of water. The reaction became exothermic and was controlled below 40°. The reaction was allowed to stand overnight. The aqueous layer was decanted and the residual semisolid was extracted with 6000 ml of refluxing hexane. The hexane was cooled and the resulting precipitate was filtered and air dried to yield 16 g (18%) of p-(5-acetyl-2-furyl)benzonitrile. An analytical sample was prepared by recrystallizing a sample from hexane/charcoal, m.p. 115°–116°.

Anal. Calcd. for $C_{13}H_9NO_2$: C, 73.92; H, 4.29; N, 6.63. Found: C, 73.93; H, 4.30; N, 6.64.

B. To a solution of 2.1 g (0.01 mole) of p-(5-acetyl-2-furyl)benzonitrile and 40 ml of 95% dioxane/water was added portionwise 0.37 g (0.10 mole) of NaBH$_4$ while maintaining the temperature at 15°–20° by means of an ice bath. The reaction was stirred at room temperature for 3 hours and then added to ice/water with a precipitate forming. The precipitate was filtered and dried in vacuum pistol at room temperature to yield 1.6 g (75%), n.p. 79°–82°, of title compound.

Anal. Calcd. for $C_{13}H_{11}NO_2$: C, 73.22; H, 5.20; H, 6.57. Found: C, 73.08; H, 5.09; N, 6.78.

EXAMPLE VIII

α-Chloromethyl-5-(p-nitrophenyl)furfuryl Alcohol

A. Sulfuryl chloride (10 ml, 0.12 mole) was added dropwise to a stirred mixture of 23 g (0.10 mole) of methyl 5-(p-nitrophenyl)-2-furyl ketone in 150 ml of chloroform at room temperature over 5 minutes. The resulting orange brown solution was stirred at ambient temperature for 1 hour, heated under reflux for 2 hours, and allowed to stand overnight. The solid which was deposited was collected by filtration and washed with chloroform to give 16 g (60%) of chloromethyl 5-(p-nitrophenyl)-2-furylketone. Two recrystallizations from ethanol gave an analytical sample, m.p. 172°–175°.

B. Sodium borohydride (1.6 g, 0.043 mole) was added in portions to a stirred mixture of 11.5 g (0.043 mole) of chloromethyl 5-(p-nitrophenyl)-2-furyl ketone in 150 ml of absolute methanol over 10 minutes at 15°–20°. The resulting solution was stirred at ambient temperature for 2.5 hours, poured into a mixture of ice and water (400 ml), and made acidic with 5% aqueous HCl. The yellow solid was collected by filtration and washed with water to give 11.5 g (100%) of title compound. Recrystallization from a MeOH—H$_2$O mixture gave an analytical sample, m.p. 111°–113°.

Anal. Calcd. for $C_{12}H_{10}ClNO_4$: C, 53.84; H, 3.76; N, 5.23. Found: C, 54.06; H, 3.85; N, 5.16.

EXAMPLE IX

1-[5-(p-Chlorophenyl)-2-furyl]-1-propanol

A. To a solution of 133 g (1.0 mole) of AlCl$_3$ in 750 ml of CS$_2$ was added 93 g (1.0 mole) of propionyl chloride. A solution of 178 g (1.0 mole) of 2-(p-chlorophenyl)furan in 500 ml of CS$_2$ was added dropwise while maintaining the temperature between 10°–15° by means of an ice bath with large volumes of HCl gas being given off. The reaction mixture was stirred in an ice bath for 15 minutes, at room temperature for 15 minutes, and then added to 2000 ml of ice/water. The aqueous layer was separated from the CS$_2$ layer and extracted with 2 × 500 ml portions of dichloromethane. The CS$_2$ and CH$_2$Cl$_2$ layers were combined and washed with 1000 ml of 6% sodium carbonate solution, with 1000 ml of water and then dried over magnesium sulfate. The solvent was removed on a Calab evaporator, and the residual oil was distilled under reduced pressure to yield 84 g of an oil which solidified on cooling, b.p. 250°–270° at 0.5–1.5 mm. The 84 g was recrystallized from hexane/charcoal and dried to yield 64 g (27.4%) of 1-[5-(p-chlorophenyl)-2-furyl]-1-propanone. An analytical sample was prepared by recrystallizing a sample a second time from hexane, m.p. 66°–68°C.

Anal. Calcd. for $C_{13}H_{11}ClO_2$: C, 66.53; H, 4.72. Found: C, 66.51; H, 4.65.

B. To a stirring solution of 34 g (0.15 mole) of 1-[5-(p-chlorophenyl)-2-furyl]-1-propanone in 300 ml of anhydrous methanol was added portionwise 4.1 g (0.11 mole) of NaBH$_4$ while maintaining the temperature between 15°–20°. The reaction solution was stirred at room temperature for 3 hours and after standing overnight was added to ice/water with a solid forming. The solid was filtered and air-dried to yield 34 g (99%) of title compound. An analytical sample was prepared by recrystallizing a sample from hexane/charcoal, m.p. 74°–75°C.

Anal. Calcd. for $C_{13}H_{13}ClO_2$: C, 65.96; H, 5.54. Found: C, 66.09; H, 5.53.

What is claimed is:

1. A compound of the formula:

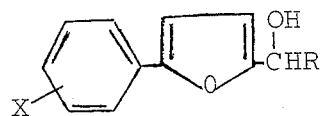

wherein X is 4-nitro, 3,4-dichloro, 3-trifluoromethyl, 4-amino, 4-acetamido, 4-methylsulfonyl, 4-cyano, or 4-chloro and R is methyl, ethyl or chloromethyl.

2. The compound 5-(4-nitrophenyl)-α-methylfurfuryl alcohol.

3. The compound 5-(3,4-dichlorophenyl)-α-methylfurfuryl alcohol.

4. The compound 5-(3-trifluoromethylphenyl)-α-methylfurfuryl alcohol.

5. The compound 5-(4-aminophenyl)-α-methylfurfuryl alcohol.

6. The compound 5-(4-acetamidophenyl)-α-methylfurfuryl alcohol.

7. The compound 5-(4-methylsulfonylphenyl)-α-methylfurfuryl alcohol.

8. The compound 5-(4-cyanophenyl)-α-methylfurfuryl alcohol.

9. The compound 5-(4-nitrophenyl)-α-chloromethylfurfuryl alcohol.

10. The compound 5-(4-chlorophenyl)-α-ethylfurfuryl alcohol.

* * * * *

UNITED STATES PATENT OFFICE
CERTIFICATE OF CORRECTION

Patent No. 3,931,247  Dated January 6, 1976

Inventor(s) Stanford S. Pelosi, Jr.

It is certified that error appears in the above-identified patent and that said Letters Patent are hereby corrected as shown below:

Structural formula in column 1 should be:

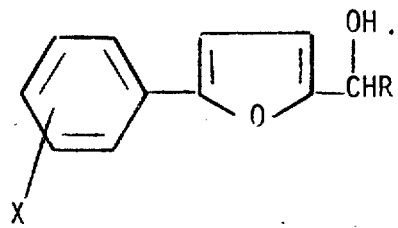

Column 5, line 11: "n.p." should be --m.p.--

Column 5, line 12: the last "H" on the line should be --N--

Signed and Sealed this first Day of June 1976

[SEAL]

Attest:

RUTH C. MASON  
Attesting Officer

C. MARSHALL DANN  
Commissioner of Patents and Trademarks